United States Patent [19]

Schnatterer et al.

[11] Patent Number: 5,760,247
[45] Date of Patent: Jun. 2, 1998

[54] PROCESS FOR THE PREPARATION OF CARBAZOLE

[75] Inventors: Albert Schnatterer; Helmut Fiege. both of Leverkusen; Joerg-Dietrich Jentsch. Mülheim; Eberhard Zirngiebl. Köln, all of Germany

[73] Assignee: Bayer Aktiengesellschaft. Leverkusen, Germany

[21] Appl. No.: 859,625

[22] Filed: May 20, 1997

[30] Foreign Application Priority Data

May 24, 1996 [DE] Germany ............ 196 20 990.0

[51] Int. Cl.$^6$ .................. C07D 209/84; C07C 211/00
[52] U.S. Cl. .................. 548/446; 564/433
[58] Field of Search ............ 548/446; 564/433

[56] References Cited

U.S. PATENT DOCUMENTS 2,921,942  1/1960  Grotta ........................ 260/315
3,041,349  6/1962  Bearse et al.

FOREIGN PATENT DOCUMENTS 860554  2/1961  United Kingdom.

OTHER PUBLICATIONS

Ullmann's Encyclopedia of Industrial Chemistry, 5th Ed., vol. A (1986) pp. 59–60.

Chemical Abstracts, vol. 110, No. 13, Mar. 27, 1989, Columbus, Ohio, US; Abstract No. 114620x, XP002037761, *Zusammendfassung* & Khim. Geterotsikl. Soedin., Bd. 5, 1988, Seiten 617–619, V.A. Tarasevich, et al.

Chemical Abstracts, vol. 101, No. 1, Jul. 2, 1984, Columbus, Ohio, US; Abstract No. 6785k, XP002037762, *Zusammendfassung* & Indian J. Chem., Sect. B, Bd. 22B, No. 12, 1983, Seiten 1191–1193, P.L. Majumder, et al.

Chemical Abstracts, vol. 84, No. 11, Mar. 15, 1976, Columbus, Ohio, US; Abstract No. 74026u, XP002037763, *Zusammendfassung* & Journal of Organic Chemistry, Bd. 40, No. 9, 1975, Easton, US, Seiten 1365–1367, B. Akermark, et al.

Database WPI, Week 9624, Derwent Publications Ltd., London, GB; AN 96–236049, XP002037764 & JP 08 092 213 A (Osaka Gas Co., Ltd.), Apr. 9, 1996, *Zusammenfassung*.

Kirk–Othmer: "Encyclopedia of chemical technology (4th Ed., vol. 2)", 1992, John Wiley and Sons, XP002037760, *Seite 458*.

*Primary Examiner*—Johann Richter
*Assistant Examiner*—Dominic Keating
*Attorney, Agent, or Firm*—Sprung Kramer Schaefer & Briscoe

[57] ABSTRACT

Diphenylamine can be dehydrocyclized on noble metal catalysts in the liquid phase at temperatures of 200° to 340° C. The reaction proceeds with a surprisingly high selectivity.

5 Claims, No Drawings

PROCESS FOR THE PREPARATION OF CARBAZOLE

The invention relates to the preparation of carbazole by the dehydrogenating cyclization of diphenylamine in the liquid phase.

Carbazole is an important intermediate for the preparation of dyestuffs, pigments, pesticides and polymers.

High temperature coal tar contains an average of 1.5% by weight of carbazole. In the distillation of tar it is enriched in the anthracene oil fraction and can be isolated from the mother liquors after crystallization of the anthracene. The industrial demand for carbazole has hitherto been satisfied predominantly from this source (Ullmann's Encyclopedia of Industrial Chemistry, 5th Edition, Volume A 5, 1986, p. 59). However, this type of process is coupled with an enormous unavoidable incidence of accompanying substances; as well as anthracene and carbazole, anthracene oil from tar distillation also contains enriched amounts of phenanthrene, pyrene and fluoroanthene and is therefore an unsatisfactory base for a long-term industrial supply.

Consequently there has been no lack of attempts in the past to prepare carbazole by means of specific syntheses, for example by the dehydrogenation and cyclization of diphenylamine, o-aminobiphenyl or N-cyclohexylideneaniline (Ullmann's Encyclopedia of Industrial Chemistry, 5th Edition, Volume A 5, p. 59).

The synthesis of carbazole from diphenylamine is of particular interest because of the inexpensive availability of diphenylamine. The formation of carbazole by passing diphenylamine through a glowing porcelain tube was described as long ago as 1872 (Graebe, Ber. dt. Chem. Ges. 5 (1872), 377). A variety of catalysts and reaction conditions for the gas phase dehydrogenation and cyclization of diphenylamine have since been published, for example platinum on charcoal (Zelinsky; Titz; Graverdoskaja; Ber. dt. Chem. Ges. 59 (1926), 2592), zinc oxide on aluminium oxide, molybdenum sulphide on aluminium oxide and tungsten sulphide (DE 937 590) and platinum (U.S. Pat. No. 2,921, 942).

However, gas phase reactions have the disadvantage of requiring special equipment with a reactor and catalyst tailor-made for the particular type of reaction. Gas phase processes thus require a considerable financial investment.

This also applies particularly to the process of gas phase dehydrogenation and cyclization of diphenylamine to carbazole. As the product is high-melting (m.p. 245° C.), precautions must be taken inter alia to prevent crystallization, for example by raising reactor parts to an appropriately high temperature or by incorporating a solvent.

Surprisingly it has now been found that the dehydrogenating cyclization of diphenylamine to carbazole can also be carried out in the liquid phase, making it possible in principle for the reaction to be performed in simple stirred reactors.

The invention therefore provides a process for the preparation of carbazole from diphenylamine, characterized in that diphenylamine is brought into contact with a noble metal catalyst in the liquid phase at 200° to 340° C.

The noble metal catalyst is preferably selected from platinum, palladium and compounds thereof. It can be used in the form of the metals, for example finely divided as platinum black or palladium black, or in the form of compounds of these metals, for example as a metal salt or metal complex. Such practical forms of the noble metal can also be applied to supports.

Preferred noble metal compounds include for example the platinum compounds $PtO_2$, $H_2PtCl_6$, $PtCl_2$, $PtCl_4$, $PtBr_2$, $Pt(NH_3)_2(NO_2)_2$, $PtI_2$, $Pt(NH_3)_4Cl_2$ and $Pt(H_2NCH_2CH_2NH_2)_2Cl_2$ and the palladium compounds PdO, $PdSO_4$, $PdBr_2$, $PdCl_2$, $Pd(CH_3CO_2)_2$, $Pd(NH_3)_4(NO_3)_2$, palladium(II) acetylacetonate and palladium(II) trifluoroacetate.

Suitable catalyst supports are any catalyst supports conventionally used in industry, e.g. those based on charcoal, oxides of elements, carbides of elements or salts of elements in various practical forms. Examples of catalyst supports based on oxides of elements are silicon dioxide (natural or synthetic silicic acids, quartz), aluminium oxide ($\alpha,\gamma$-$Al_2O_3$), clays, natural and synthetic aluminosilicates (zeolites), titanium dioxide (rutile, anatase), zirconium dioxide or zinc oxide. Preferred carbides and salts of elements include silicon carbide, aluminium phosphate, barium sulphate, calcium carbonate and the like. They can be used either as chemically homogeneous pure substances or in a mixture. Both lumpy and pulverulent materials are suitable as catalyst supports according to the invention.

The noble metal can be applied to the catalyst support by methods which are known in principle. Thus one or more noble metal compounds can be applied to the catalyst support for example by steeping, absorption, dipping, spraying, impregnation and ion exchange. It is also possible to fix the metals to the support by precipitation with a base. Examples of suitable bases are alkali metal (alkaline earth metal) hydroxides such as calcium, magnesium, sodium, lithium and potassium hydroxide, alkali metal (alkaline earth metal) hydrogen carbonates such as calcium, magnesium, sodium, lithium and potassium hydrogen carbonate, alkali metal (alkaline earth metal) carbonates such as calcium, magnesium, sodium, lithium and potassium carbonate, and alkali metal salts of weak acids (e.g. acetic acid), such as sodium and potassium acetate.

The noble metal catalysts can either be used directly in the form of the metal compounds, optionally on one of said supports, or reduced prior to use. Examples of suitable reducing agents are hydrazine, formaldehyde, sodium formate and sodium borohydride at temperatures of 0° to 200° C., or gaseous hydrogen at temperatures of 0° to 500° C., preferably 20° to 300° C.

It is preferable to use supported catalysts and particularly preferable to use supported platinum and platinum compounds.

The concentration of noble metal (noble metal compound) on the support is preferably 0.1 to 15% by weight, especially 0.5 to 10% by weight, based on the sum of support and noble metal (noble metal compound) calculated as the metal.

The noble metal catalyst is used in amounts of 0.001 to 2% by weight, preferably 0.01 to 1% by weight, calculated as the metal and based on diphenylamine.

The process according to the invention is preferably carried out at a temperature of 220° to 310° C., especially 240° to 300° C.

There are a variety of ways of carrying out the process according to the invention in industrial plants. In the simplest embodiment the diphenylamine (m.p. 52° C., b.p. 302° C.) and the catalyst are brought to the reaction temperature, for example with stirring in a reactor suitable for handling liquids. A diluent is not necessary for the process but can simplify the handling of the reaction mixture.

Suitable diluents are basically any high-boiling organic compounds and mixtures of compounds which are liquid over a sufficient temperature range and have an adequate stability under the reaction conditions. Examples of suitable inexpensive diluents are isomeric terphenyls, isomeric diisopropylnaphthalenes, isomeric ditolyl ethers, polyethylene glycol, biphenyl and diphenyl ether.

The pressure in the process according to the invention is not subject to any specific restriction. As the reaction releases hydrogen, it may be advantageous to keep the pressure level low. It may also be useful to reduce the pressure slightly.

However, the process is preferably carried out in the region of atmospheric pressure.

The liberated hydrogen can be removed as off-gas, but it can also be transferred to suitable acceptors in the manner of a hydrogen transfer reaction. Removal of the hydrogen can also be accelerated by passing an inert gas stream, for example consisting of nitrogen or carbon dioxide, through the reaction mixture.

Surprisingly the dehydrocyclization of diphenylamine to carbazole by the process according to the invention also takes place successfully in the liquid phase with a high reaction rate. Because of the comparatively long residence time of the reaction mixture in the liquid phase and the associated thermal stress, it could not be expected that carbazole would be formed with such a high selectivity.

EXAMPLES

The percentages are by weight in the following Examples.

Example 1

100 g of diphenylamine and 10 g of 5% Pt/charcoal (K-0101 from Haereus, 50% water) were placed in a 250 ml glass round-bottomed flask equipped with a thermometer and a distillation bridge. After the apparatus had been flushed with nitrogen, the mixture was heated for 5 hours at 290° C., with stirring. 13 g of low-boiling components distilled off in the process, being mainly water (from the catalyst), benzene and some aniline.

After cooling, the residue was taken up with 400 ml of acetone, the catalyst was filtered off and the filtrate was evaporated to leave a residue of 86.6 g of a crystalline solid containing the following (GC):

10.2% of aniline
39.4% of diphenylamine
45.1% of carbazole.

This corresponds to a carbazole selectivity of 60.0% with a diphenylamine conversion of 65.9%.

Example 2

200 g of diphenylamine and 10 g of 1% Pt/γ-$Al_2O_3$ were placed in a 0.7 l VA steel reactor equipped with a water-cooled condenser. After the reactor had been flushed with nitrogen, the mixture was heated for 5 hours at 250° C., with stirring and without the use of pressure. 2.6 g of low-boiling components were separated off during the reaction phase. After cooling, the reaction mixture was taken up with 400 ml of acetone, the catalyst was filtered off and the filtrate was evaporated to leave a residue of 192.8 g of a crystalline solid containing the following (GC):

0.8% of aniline
91.4% of diphenylamine
5.8% of carbazole.

This corresponds to a carbazole selectivity of 47.6% with a diphenylamine conversion of 11.9%.

We claim:
1. A process for the preparation of carbazole from diphenylamine, wherein diphenylamine is brought into contact with a noble metal catalyst in the liquid phase at 200° to 300° C.
2. The process according to claim 1, wherein the noble metal catalyst is selected from the group consisting of platinum, palladium $PtO_2$, $H_2PtCl_6$, $PtCl_2$, $PtCl_4$, $PtBr_2$, $Pt(NH_3)_2(NO_2)_2$, $PtI_2$, $Pt(NH_3)_4Cl_2$, $Pt(H_2NCH_2CH_2NH_2)_2Cl_2$, PdO, $PdSO_4$, $PdBr_2$, $PdCl_2$, $Pd(CH_3CO_2)_2$, $Pd(NH_3)_4(NO_3)_2$, palladium(II) acetylacetonate and palladium (II) trifluoroacetate.
3. The process according to claim 1, wherein the noble metal catalyst is used on a catalyst support.
4. The process according to claim 3, wherein platinum is used as the noble metal catalyst and charcoal, aluminum oxide or silicon dioxide is used as the catalyst support.
5. The process according to claim 1, wherein said process is carried out in the temperature range of 220° to 310° C.

* * * * *

UNITED STATES PATENT AND TRADEMARK OFFICE
CERTIFICATE OF CORRECTION

PATENT NO : 5, 760, 247
DATED : June 2, 1998
INVENTOR(S) : Schnatterer, et al.

It is certified that error appears in the above-identified patent and that said Letters Patent is hereby corrected as shown below:

Title Page, [22] "Filed"    Delete " May 20, 1997 " and substitute --- May 19, 1997 ---

Signed and Sealed this

Sixth Day of June, 2000

Attest:

Q. TODD DICKINSON

*Attesting Officer*   *Director of Patents and Trademarks*